US010098707B2

(12) United States Patent
Kubiak et al.

(10) Patent No.: US 10,098,707 B2
(45) Date of Patent: Oct. 16, 2018

(54) SURGICAL POSITIONING SYSTEM, APPARATUS AND METHOD OF USE

(71) Applicant: OrthoGrid Systems, Inc., Salt Lake City, UT (US)

(72) Inventors: Erik Noble Kubiak, Salt Lake City, UT (US); Richard Boddington, Sal Lake City, UT (US); Edouard Saget, Salt Lake City, UT (US)

(73) Assignee: Orthogrid Systems Inc., Salt Lake City, UT (US)

( * ) Notice: Subject to any disclaimer, the term of this patent is extended or adjusted under 35 U.S.C. 154(b) by 22 days.

(21) Appl. No.: 15/305,853

(22) PCT Filed: Aug. 17, 2015

(86) PCT No.: PCT/US2015/045590
§ 371 (c)(1),
(2) Date: Oct. 21, 2016

(87) PCT Pub. No.: WO2017/030557
PCT Pub. Date: Feb. 23, 2017

(65) Prior Publication Data
US 2017/0215985 A1    Aug. 3, 2017

(51) Int. Cl.
*A61B 90/00*    (2016.01)
*A61B 6/00*    (2006.01)
(Continued)

(52) U.S. Cl.
CPC ............ *A61B 90/39* (2016.02); *A61B 6/0492* (2013.01); *A61B 6/4405* (2013.01); *A61B 6/461* (2013.01);
(Continued)

(58) Field of Classification Search
CPC ......... A61B 90/39; A61B 90/06; A61B 90/37; A61B 6/4405; A61B 6/461; A61B 6/5258; A61B 6/0492; A61B 46/10
See application file for complete search history.

(56) References Cited

U.S. PATENT DOCUMENTS 3,569,994 A * 3/1971 Rau .................. G01C 21/20
235/61 NV
3,609,299 A * 9/1971 Wright ................. G06G 1/0052
235/61 NV
(Continued)

OTHER PUBLICATIONS

PCT written opinion of the internal preliminary examination due Sep. 29, 2016.

*Primary Examiner* — Bo J Peng
(74) *Attorney, Agent, or Firm* — Veritay Group IP; Susan Fentress

(57) ABSTRACT

A surgical positioning system is provided that includes a dimensioned grid having a plurality of dimensioned radio-opaque lines corresponding to surgical variables and a substrate connected to or integral with the grid. This system is used to obtain subject specific data from an image of a subject obtained during a surgical procedure by following the steps of: providing a grid having a plurality of dimensioned radio-opaque lines relating to surgical variables; placing the subject on a substrate; and obtaining subject specific data from an image of said subject. This invention relates to an apparatus made of a grid having a plurality of dimensioned radio-opaque lines relating to surgical variables and a sealable container sized to receive the dimensioned grid.

10 Claims, 18 Drawing Sheets

(51) Int. Cl.
*A61B 6/04* (2006.01)
*A61B 46/10* (2016.01)

(52) U.S. Cl.
CPC ............ *A61B 6/5258* (2013.01); *A61B 46/10* (2016.02); *A61B 90/06* (2016.02); *A61B 90/37* (2016.02)

(56) References Cited

U.S. PATENT DOCUMENTS

| | | | |
|---|---|---|---|
| 3,770,956 | A | 11/1973 | Johnson |
| 4,918,715 | A | 4/1990 | Krupnick et al. |
| 4,985,019 | A | 1/1991 | Michelson |
| 5,020,088 | A | 5/1991 | Tobin |
| 5,030,223 | A | 7/1991 | Anderson et al. |
| 5,052,035 | A | 9/1991 | Krupnick |
| 5,105,457 | A | 4/1992 | Glassman |
| 5,285,785 | A | 2/1994 | Meyer |
| 5,550,378 | A * | 8/1996 | Skillicorn ............... A61B 6/06 250/367 |
| 5,690,108 | A * | 11/1997 | Chakeres ............ A61B 6/0442 378/20 |
| 6,159,221 | A | 12/2000 | Chakeres |
| 6,285,902 | B1 | 9/2001 | Kienzle |
| 6,690,767 | B2 | 2/2004 | Davis |
| 6,697,664 | B2 | 2/2004 | Kienzle et al. |
| 6,714,628 | B2 | 3/2004 | Broyles et al. |
| 6,723,097 | B2 | 4/2004 | Fraser et al. |
| 6,739,752 | B2 * | 5/2004 | Sabczynski ............ A61B 6/583 378/189 |
| 6,827,723 | B2 * | 12/2004 | Carson .................. A61B 34/20 606/130 |
| 6,928,146 | B2 | 8/2005 | Broyles et al. |
| 7,127,826 | B2 | 10/2006 | Russell |
| 7,337,946 | B2 * | 3/2008 | Belton .................... G06G 1/08 235/61 R |
| 7,482,601 | B2 | 1/2009 | Lewis et al. |
| 7,508,919 | B2 | 3/2009 | Young et al. |
| 7,853,311 | B1 | 12/2010 | Webb |
| D664,661 | S | 7/2012 | Kubiak et al. |
| 8,280,490 | B2 | 10/2012 | Pfeiler |
| 8,526,700 | B2 | 9/2013 | Isaacs |
| 8,577,115 | B2 | 11/2013 | Gering et al. |
| 8,611,504 | B2 | 12/2013 | Kubiak et al. |
| 8,611,697 | B2 | 12/2013 | Nathaniel et al. |
| 8,718,346 | B2 | 5/2014 | Isaacs et al. |
| 8,792,704 | B2 | 7/2014 | Isaacs |
| 8,908,952 | B2 | 12/2014 | Isaacs et al. |
| 9,109,996 | B2 | 8/2015 | Nathaniel et al. |
| 9,111,180 | B2 | 8/2015 | Rappaport et al. |
| 9,119,572 | B2 | 9/2015 | Gorek et al. |
| 2003/0114752 | A1 * | 6/2003 | Henderson ............ A61B 19/52 600/433 |
| 2003/0114862 | A1 * | 6/2003 | Chu ...................... A61B 90/11 606/130 |
| 2004/0015176 | A1 | 1/2004 | Cosman |
| 2004/0068187 | A1 | 4/2004 | Krause et al. |
| 2004/0076261 | A1 | 4/2004 | Broyles et al. |
| 2004/0103903 | A1 | 6/2004 | Falahee |
| 2004/0255383 | A1 | 12/2004 | Longton |
| 2005/0288691 | A1 * | 12/2005 | Leiboff ................ A61F 2/0063 606/151 |
| 2006/0065273 | A1 | 3/2006 | Lewis |
| 2008/0167550 | A1 | 7/2008 | Weiser et al. |
| 2009/0129556 | A1 | 5/2009 | Ahn |
| 2009/0226060 | A1 | 9/2009 | Gering et al. |
| 2009/0285366 | A1 | 11/2009 | Essenreiter et al. |
| 2010/0041979 | A1 | 2/2010 | Harter |
| 2010/0086185 | A1 | 4/2010 | Weiss |
| 2011/0191084 | A1 | 8/2011 | Cooke |
| 2001/3009482 | | 4/2013 | Lalena |
| 2013/0094628 | A1 | 4/2013 | Lalena et al. |
| 2013/0304203 | A1 * | 11/2013 | Beer ...................... A61F 2/1624 623/6.37 |
| 2014/0093154 | A1 | 4/2014 | Penenberg |
| 2014/0128717 | A1 | 5/2014 | Lytle et al. |

\* cited by examiner

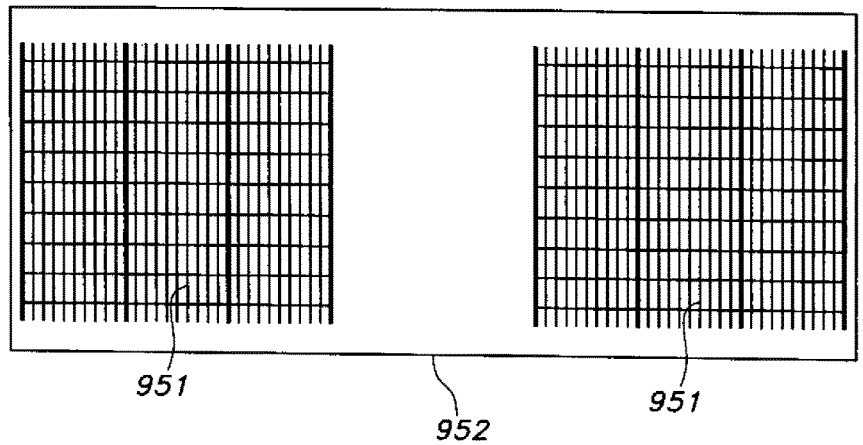
FIG. 19
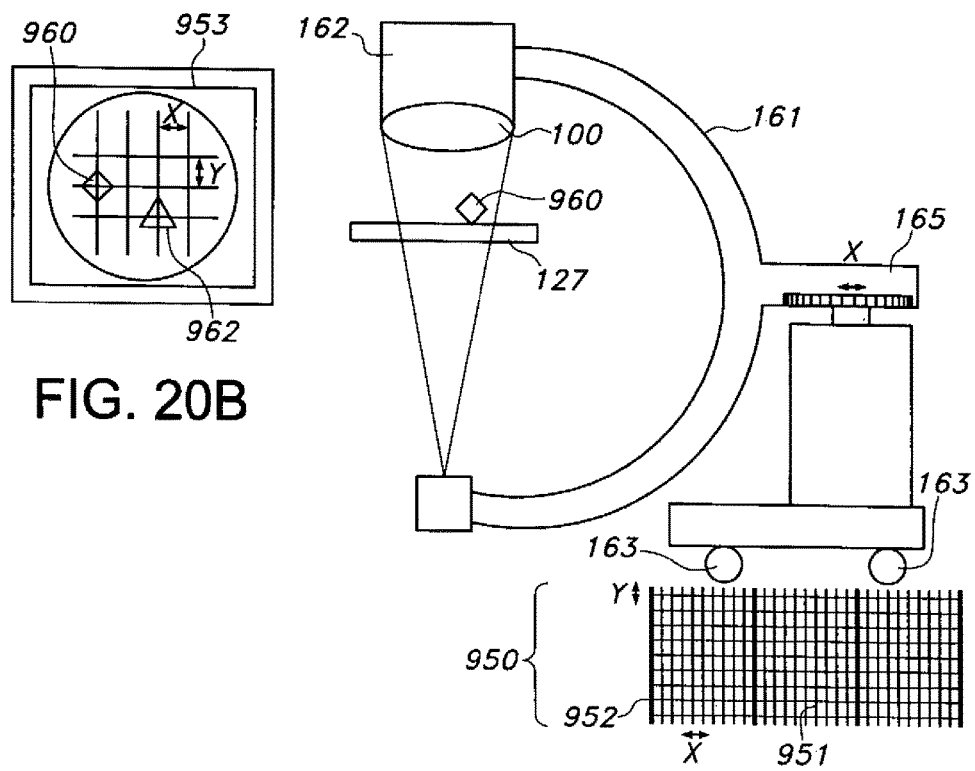
FIG. 20B
FIG. 20A

SURGICAL POSITIONING SYSTEM, APPARATUS AND METHOD OF USE

FIELD OF THE INVENTION

The present invention relates to a surgical positioning system and method to use this apparatus in various surgical applications, such as, for example a total hip arthroplasty or trauma fracture and deformity correction.

BACKGROUND OF THE INVENTION

Many of the radiographic parameters essential to total hip arthroplasty (THA) component performance, such as wear, and stability, can be assessed intraoperatively with fluoroscopy. However even with intraoperative fluoroscopic guidance, the placement of an implant may still not be as close as desired by the surgeon. For example, malpositioning of the acetabular component during hip arthroplasty can lead to problems. For the acetabular implant to be inserted in the proper position relative to the pelvis during hip arthroplasty requires that the surgeon know the position of the patient's pelvis during surgery. Unfortunately, the position of the patient's pelvis varies widely during surgery and from patient to patient.

Various devices have been suggested to reduce malpositioning of these surgical components. For example, a transverse acetabular ligament has been suggested as a qualitative marker of the orientation of the acetabulum. (Archbold H A, of al., The Transverse Acetabular Ligament; an Aid to Orientation of the Acetabular Component During Primary Total Hip Replacement a Preliminary Study of 1000 Cases Investigating Postoperative Stability, J Bone Joint Surg BR, 1906 July; 88(7):883-7. However, it has been suggested that the acetabulum may be deteriorated due to arthritis. Others have proposed using a tripod device that uses the anatomy of the ipsilateral hemi pelvis as the guide to position the prosthetic acetabular component. U.S. Patent Publication Number 19090306679. This instrument has three points. The first leg is positioned in the area of the posterior inferior acetabulum, a second leg is positioned in the area of the anterior superior iliac scetral axise and a third leg is positioned on the ileum of the subject. U.S. Patent Publication Number 19090306679. However, a need exists in the industry for a device that is not implantable or invasive and is adaptable to a variety of applications.

SUMMARY OF THE INVENTION

A surgical positioning system includes a movable dimensioned grid having a plurality of dimensioned radio-opaque patterns corresponding to a plurality of surgical variables and a substrate connected to or integral with the movable dimensioned grid to facilitate movement over an object being imaged during a procedure and an image of the movable dimensioned providing coordinate data.

In another embodiment, a movable grid device is provided. The movable device is made of: an inner section, the inner section can allow for removable grid inserts, the inner section of the movable grid has a plurality of dimensioned radio-opaque lines relating to surgical variables; a plurality of radial fixturing grips, each of the radial fixturing grips is configured to position the inner section; and a retaining member configured to retain the inner section and to attach, to an imaging device.

This invention also provides an apparatus made of a grid having a plurality of dimensioned radio-opaque lines relating to surgical variables and a sealable sterile container sized to receive or affix the grid. This embodiment simplifies the sterilization, if required of the grid between surgical applications.

In another embodiment, the substrate is a procedure room table mat and the grid is integrated into the procedure room table mat to form a dimensioned grid mat. The dimensioned grid mat has at least one aperture in a top surface sized to accommodate a positioning device. The positioning device is sized to project through and above the top surface of the dimensioned grid mat, wherein the position of a subject on the mat can be maintained in a selected position with the at least one positioning device.

In another embodiment, a disposable sterile, or non-sterile, fluoroscopic grid-drape for use intraoperatively, independent of, within, or as an integral part of C-arm drape/sleeve/cover, to determine angulation and alignment of implants and/or limbs is provided.

In another embodiment, a disposable sterile, or non-sterile, radiographic grid having the ability to attach to the C-arm image intensifier or other radiographic receiver by means of any method, such as, magnets, suction cups/devices/tapes, clamps, and straps is provided. This includes method of grid attachment to the C-arm image intensifier or image receiver or any other/sleeve/apparatus using adhesives of any type.

In another embodiment, use of radio-opaque ink methods and technology to print, spray, penning a grid pattern or use of radiographic metals, such as tungsten and steel, for use in any musculoskeletal surgical procedure are provided. The radio-opaque ink printing can be applied to, or the metals incorporated within, any suitable and appropriate substrate.

In another embodiment, a distortion correction method for an anatomical image captured from an imaging system includes the steps of: processing with an analogue or digital grid and correcting for distortion/parallax that is inherent in an imaging system. The anatomical image captured from an imaging, system is processed with an analogue or digital (software generated virtual grid) grid and corrected for distortion/parallax that is inherent in imaging systems. This distortion correction method can be any available technique and uniquely applied to the use of a grid (analogue or virtual) with this surgical positioning system.

All designs and embodiments include sterile/non-sterile, and disposable/non-disposable applications

BRIEF DESCRIPTION OF THE SEVERAL VIEWS OF THE DRAWINGS

The drawings show schematically fluoroscopic or radiographic alignment apparatus and method of use according to an example form of the present invention. The invention description refers to the accompanying drawings:

FIG. 19 is an embodiment of the invention showing an exemplary embodiment of a grid mat.

FIG. 20A is an embodiment of the invention showing an exemplary embodiment of a system.

FIG. 20B is an embodiment of the invention showing an exemplary embodiment of a grid image.

DETAILED DESCRIPTION OF THE INVENTION

The present invention may be understood more readily by reference to the following detailed description of the invention. It is to be understood that this invention is not limited to the specific devices methods, conditions or parameters described herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

These and other aspects, features and advantages of the invention will be understood with reference to the detailed description herein, and will be realized by means of the various elements and combinations particularly pointed out in the appended claims. It is to be understood that both the foregoing general description and the following detailed description of the invention are exemplary and explanatory of preferred embodiments of the inventions, and are not restrictive of the invention as claimed. Unless defined otherwise, all technical and scientific terms, used herein have the same meaning as commonly understood by one of ordinary skill in the art to which this invention belongs.

The present invention, provides an apparatus and method for determining and measuring leg length, offset, and cup position during arthroplasty surgery by using a dimensioned grid within the field of view and patient in conjunction with X-ray to measure surgical variables, such as, hip implant position to determine the relative leg length and offset measurements for the implant. Arthroplasty surgery includes, for example: hip (anterior approach), hip (posterior approach), knee, ankle, elbow, and shoulder. The present invention includes an embodiment for trauma applications. Trauma surgery includes any and all bone fractures and deformity corrections.

Figure 1:
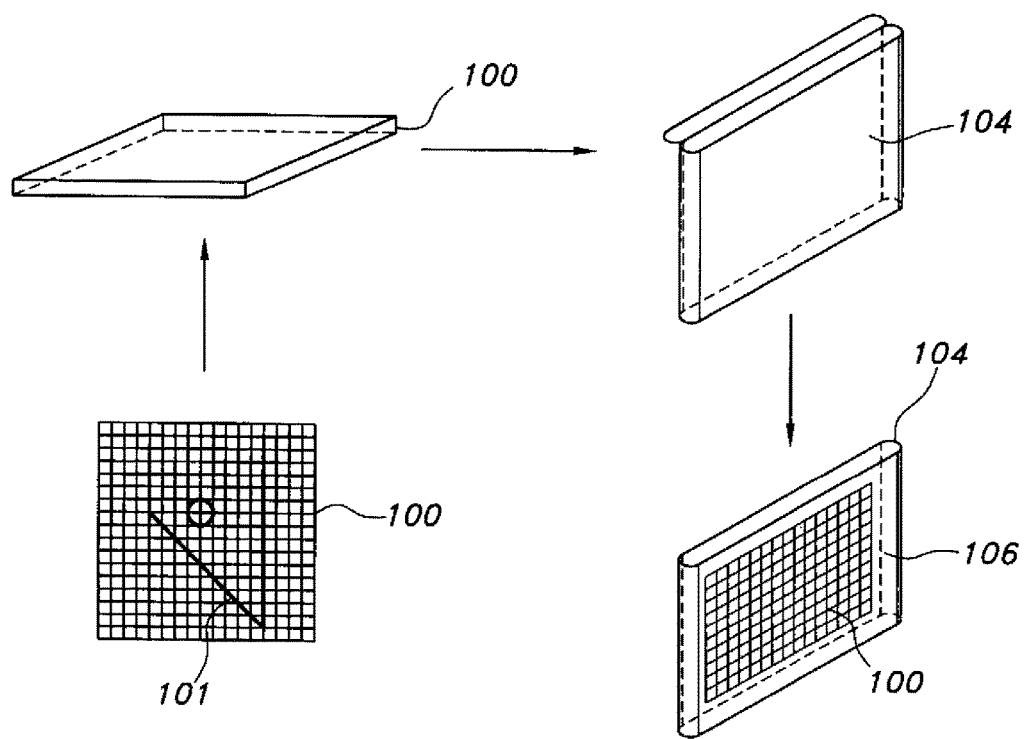
FIG. 1 is a perspective view of an exemplary embodiment of a dimensioned grid of the present invention and a view showing the sterile pouch/bag/container.
Figure 2:
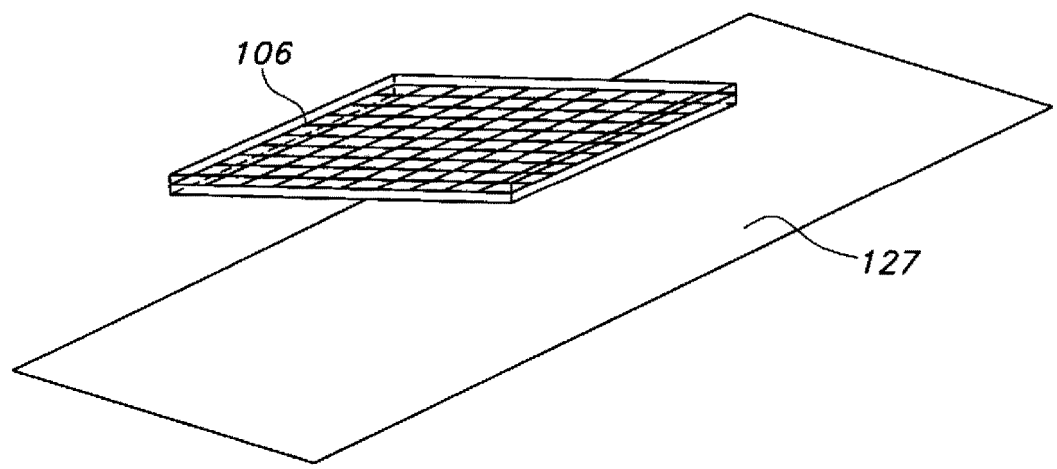
FIG. 2 is a front perspective view of a dimensioned grid within the field of view and a procedure table.
Figure 3:
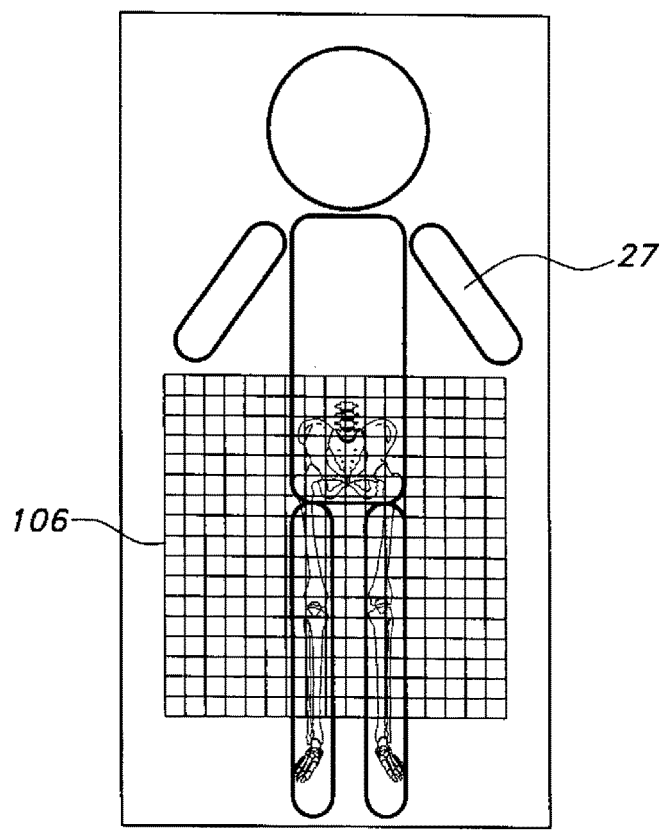
FIG. 3 is a top view of the apparatus of the present invention used in a standard X-ray image technique where the grid is placed on top of the patient and images taken as needed.

Now referring to FIGS. 1-3 an exemplary embodiment of a dimensioned grid 100 is shown. The dimensioned grid 100 has a plurality of dimensioned radio-opaque lines 101 relating to surgical variables. The portion of the dimensioned grid 100 that is not opaque is radiolucent. The dimensioned grid 100 can be referred to as a dimensioned grid 100 having a plurality of dimensioned radio-opaque lines 101. The dimensioned grid 100 can include any shape or pattern of geometric nature or text to reference angles, length positioning or targeting. The radio-opaque portion of the dimensioned grid 100 can be a single line, a geometrical pattern, number, letter or a complex pattern of multiple lines and geometries that correspond to surgical variables. The grid patterns are predesigned based upon the surgeons knowledge of anatomy and clinical experience including interpretation of morphometric literature and studies identifying key relationships and dimensions between anatomical landmarks and its application in supporting good surgical technique as it relates to specific procedures. The dimensioned grid 100 can be sterilized or use with a sealable container 104.

The dimensioned grid 100 has a plurality of dimensioned radio-opaque lines 101 relating to surgical variables. The dimensioned grid 100 is used with an object being imaged intraoperatively with an imaging system, such as for example C-arm, flat plate, CT, MRI.

The dimensioned grid 100, in one embodiment, can be placed in a sealable container 104, such as a bag or pouch that can be allowed to be used in a sterile field. This step can occur within a sterile environment during any surgical procedure. For example, the dimensioned grid 100 is placed inside a sterile pouch, bag, or container 104. The sterile pouch, bag, or container 104 can be manufactured of any suitable material. A standard X-ray container can be sealed with the dimensioned grid 100 in sterile pouch or bag 104 within.

The same protocol can be followed in a non-sterile environment before, during, and/or after any surgical event. The combination of the dimensioned grid 100 in a sterilizable material or within a sterile pouch, bag, or container 104 is referred to as the grid assembly 106. The dimensioned grid assembly 106, in one embodiment, is positioned within the field of view of the x-ray with a patient. The surgeon can adjust the dimensioned grid assembly 106 as images are taken. The dimensioned grid assembly 106 can be adjusted intraoperatively.

Figure 4:
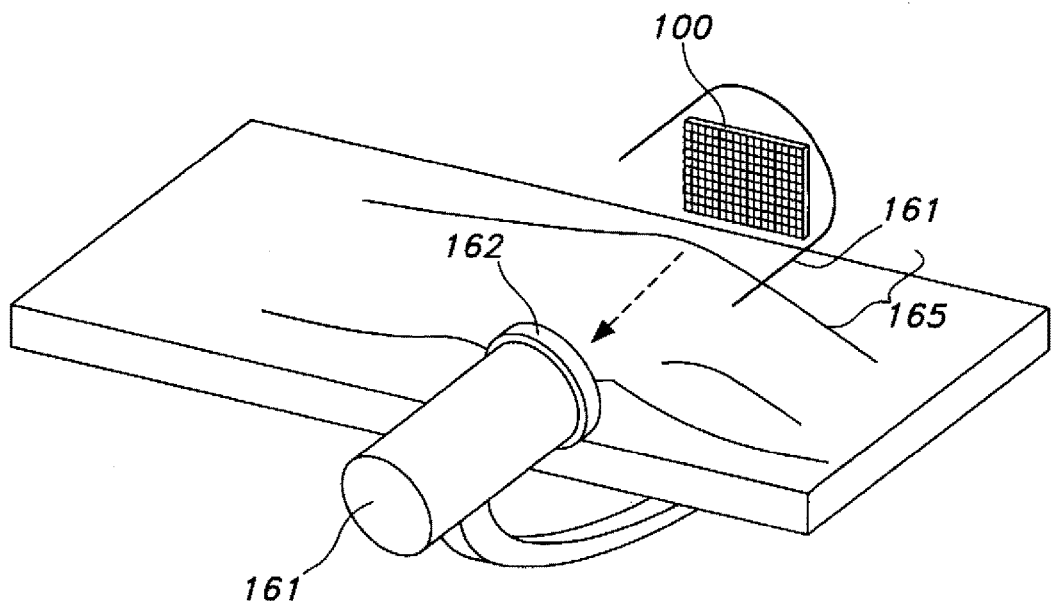
FIG. 4 is an embodiment of the invention showing an illustrative sketch showing the relationship of the patient to the apparatus in a posterior approach or in a lateral decubitus position

Now referring to FIG. 4 disposable sterile, or non-sterile, fluoroscopic grid-drape for use intraoperatively, independent of, within, or as an integral part of C-arm or imaging drape/sleeve/cover, that can be used to determine angulation and alignment of implants and/or limbs is disclosed. This embodiment to include uses for any and all musculoskeletal surgical procedures (to include: hip replacement, knee replacement, shoulder replacement, trauma fracture repair, etc.) All embodiments include any use of the dimensioned grid 100 as a disposable or reusable item.

More specifically, in a sterile environment during any surgical procedure, a dimensioned grid 100 is either sterile or incorporated into a sterile disposable C-arm or imaging sleeve, pouch, bag, cover, or container 104. The sterile sleeve, pouch, bag, cover or container 104 can be manufactured of any suitable material, such as high density polyethylene or low density polyethylene. The sleeve, pouch, bag, container 104 can be sealed with the dimensioned grid 100 enclosed within to form a grid assembly 106. The grid assembly 106 can, but is not required to, be integrated into the sleeve, pouch, bag, cover, or container 104 and placed over the C-arm image intensifier 162 in a standard, sterile manner in preparation for C-arm use. The same protocol can be followed in a non-sterile environment before, during, and/or after any surgical event.

Figure 5:
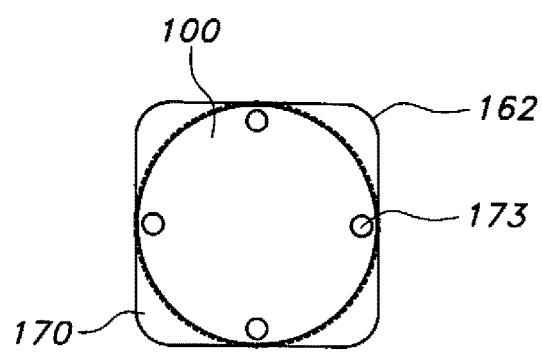
FIG. 5 is an illustrative embodiment of a disposable, or non-disposable sterile, or non-sterile, grid for use as an attachment to the C-arm device image intensifier, or any X-ray receiver, or sterile drape covering the x-ray receiver/detector
Figure 6:
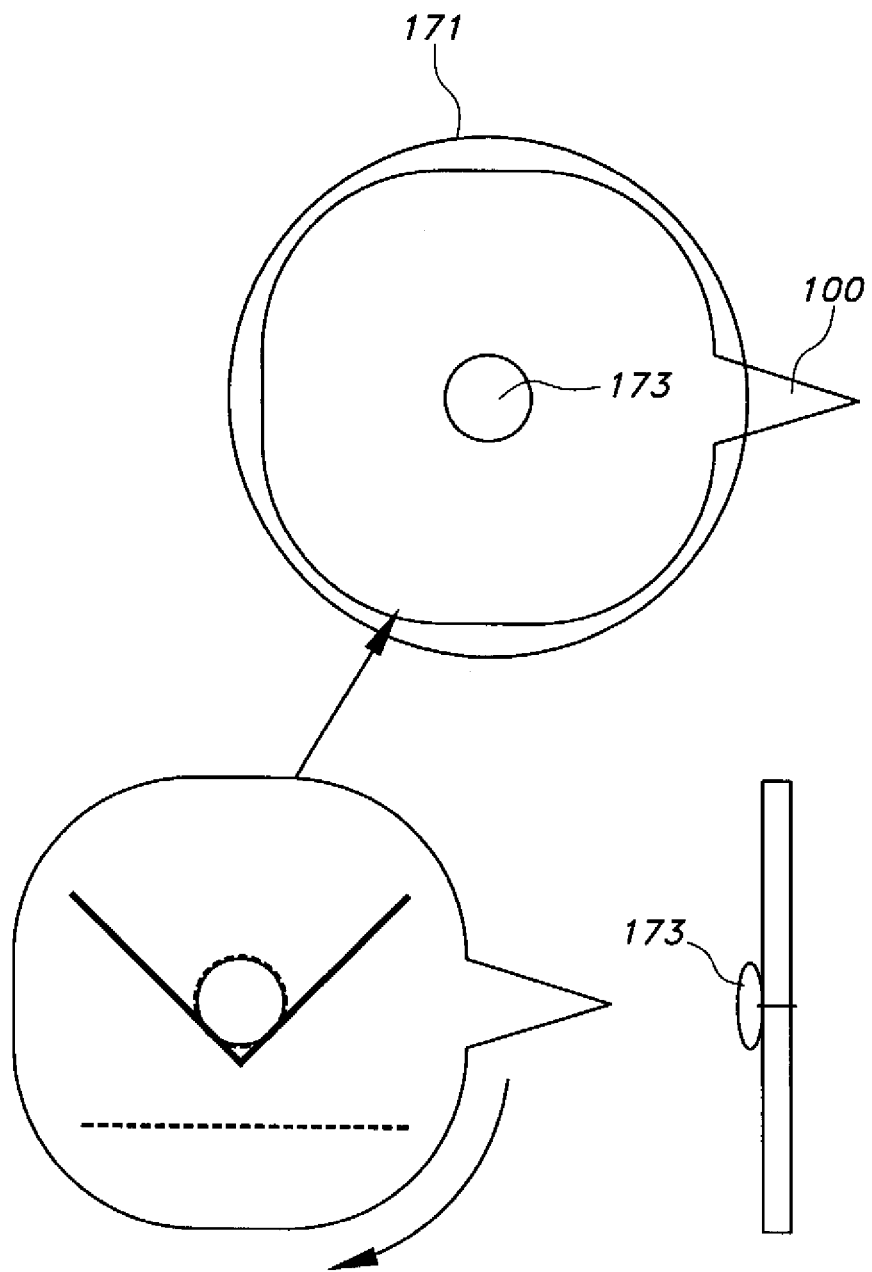
FIG. 6 is an illustrative embodiment of a disposable, or non-disposable sterile, or non-sterile, grid for use as an attachment to the C-arm device image intensifier or any X-ray receiver, or the tube is shown.

Now referring to FIGS. 5-6 a disposable, or non-disposable sterile, or non-sterile, dimensioned grid 100 for use as an attachment to an imaging device 161, such as a C-arm device, having an image intensifier 162 (or any imaging receiver) or the tube 171 is shown. In one exemplary embodiment, a disposable sterile, or non-sterile, radiographic dimensioned grid 100 is configured to attach to the image intensifier 162. The dimensioned grid 100 is attached with the use of magnets (standard or Neodymium), suction cup technology (standard, Gecko, Nano suction technology) 173, or any other means such as straps or clamps, and adhesives (glue, tape) or manually holding the dimensioned grid 100 in place against either the X-ray image intensifier/receiver or the imaging tube 170.

The dimensioned grid 100 having a plurality of dimensioned radio-opaque lines relating to surgical variables is placed in a sealable container sized to receive the dimensioned grid 100 to form a grid assembly 106; and the grid assembly 106 is positioned over the intensifier 162 of an imaging device 161.

Figure 7:
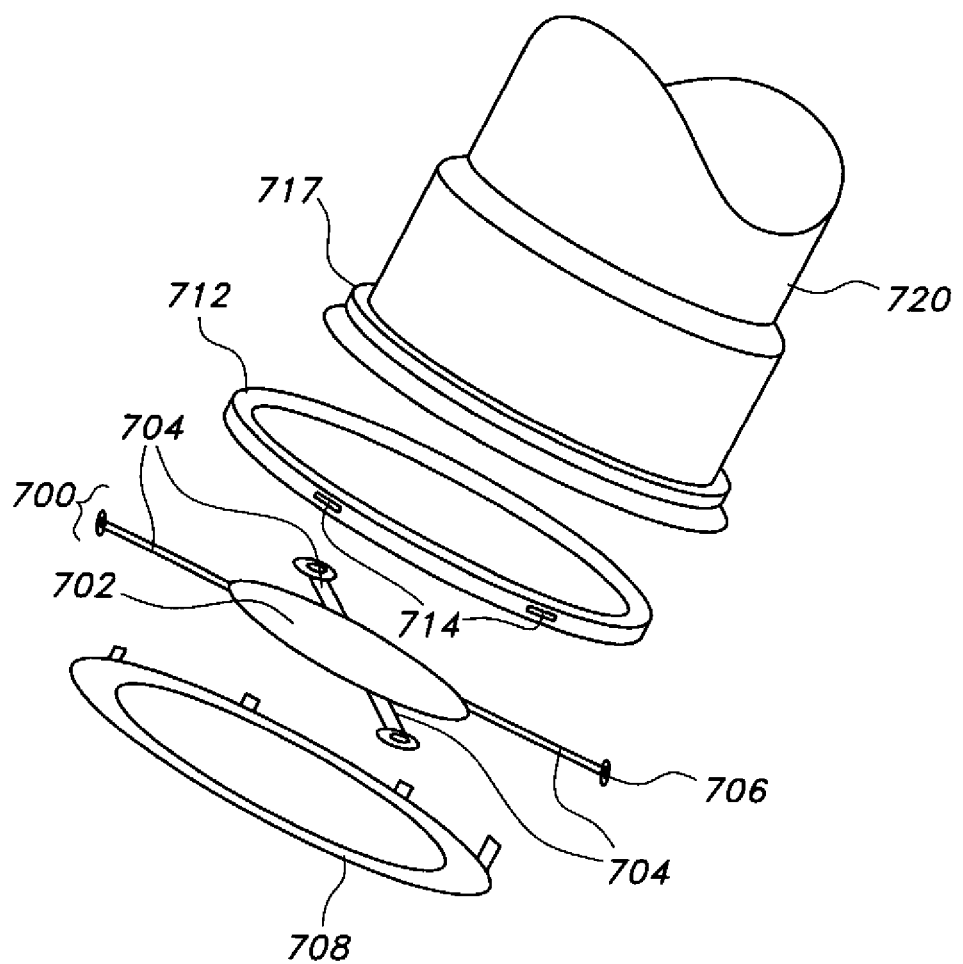
FIG. 7 is an embodiment of the invention showing an exemplary embodiment of a movable grid C arm or radiographic assembly.

Now referring to FIG. 7, an illustrative embodiment of a movable dimensioned grid 700 is shown. The movable dimensioned grid 700 is made of an inner circular section 702 having a plurality of radial fixturing grips 704 each with an enlarged end 706. The inner circular section 702 of the dimensioned grid 700 has a plurality of dimensioned lines relating to surgical variables. In one embodiment, the lines are radio-opaque.

In this embodiment, the movable dimensioned grid 700 is positioned in a substrate, such as a retaining member, that is formed of a pressing plate 706 and a rotating ring 712. The rotating ring 712 has a plurality of slots 714, each are sized to retain an enlarged end 706 having a plurality of radial fixturing grips 704 to allow planar movement of the grid 700, in several degrees of freedom of the movable dimensioned grid 700. The rotating ring 712 is affixed to fixed ring 717. The fixed ring 717 is connected to the C-arm head 720.

Figure 8:
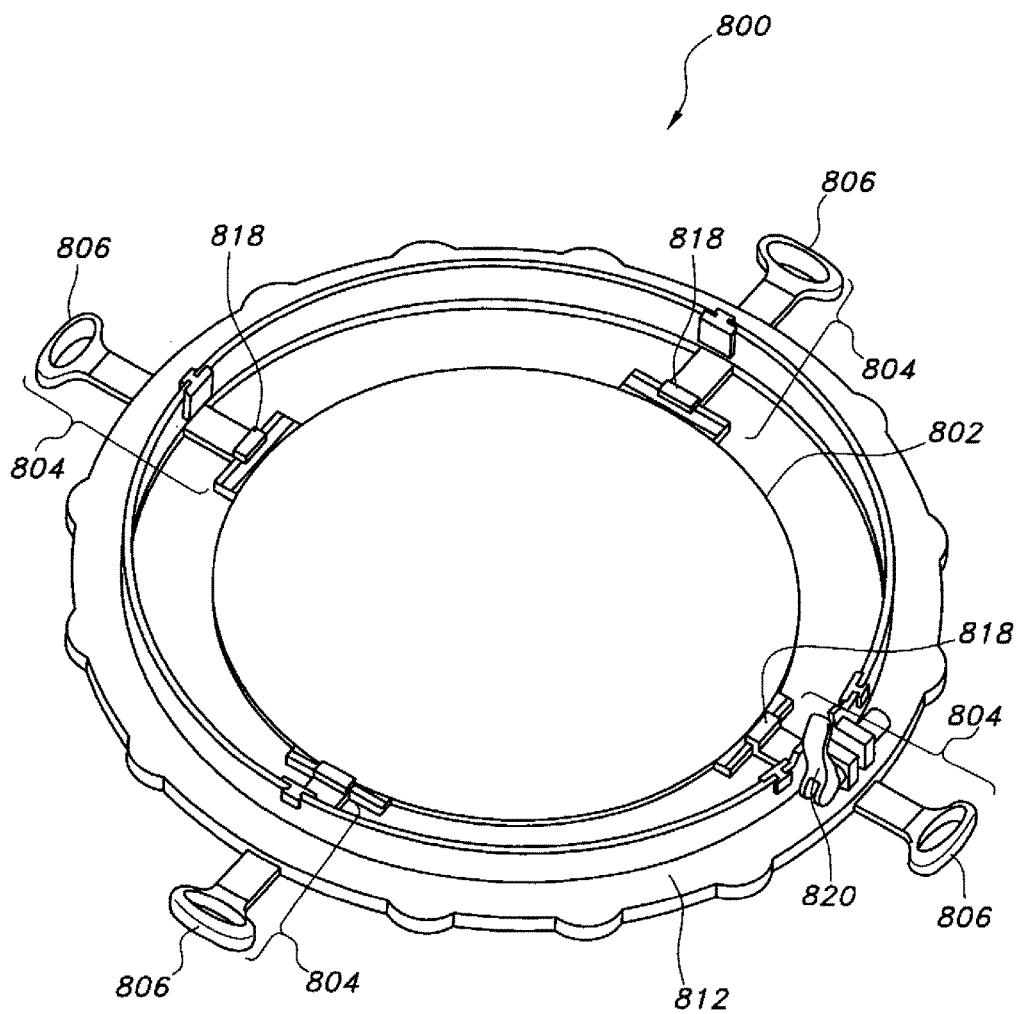
FIG. 8 is an embodiment of the invention showing an exemplary embodiment of a top perspective view of movable dimensioned grid assembly.

In another illustrative embodiment, shown in FIGS. 8-15, an exemplary embodiment, of a movable dimensioned grid assembly 800 is provided. FIG. 8 shows a top perspective view of the movable dimensioned grid assembly 800. The movable dimensioned grid assembly 800 is made of an inner circular section 802. The inner circular section 802 is positioned within a rotating ring 812. The inner section 802 is removable and allows for removable grid inserts to be added to the movable dimensioned grid assembly 800. The inner section 802 of the movable dimensioned grid assembly 800 has a plurality of dimensioned radio-opaque lines relating to surgical variables 807. The rotation ring 812 rests freely on the fixed ring 717, shown in FIG. 7, to allow for movement such as rotation, in several degrees of freedom, or translation in several millimeters, or a combination of the movable dimensioned grid assembly 800.

The inner circular section 802 is, positioned within rotating ring 812 by a plurality of radial fixturing grips 804. Each of the plurality of radial fixturing grips 804 connect to the inner circular section 802 by claw, (or clamp, grip, bracket track, rail-type system) 818.

Figure 9:
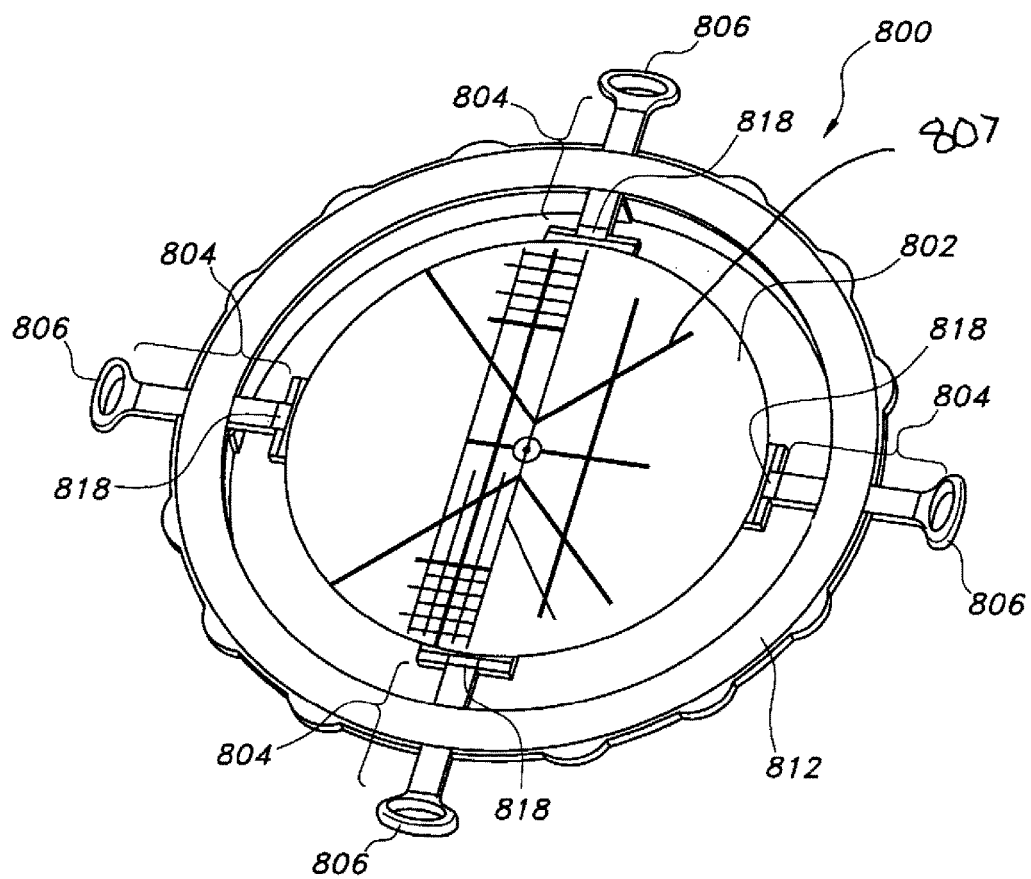
FIG. 9 is an embodiment of the invention showing a front view exemplary embodiment of a movable dimensioned grid.
Figure 10:
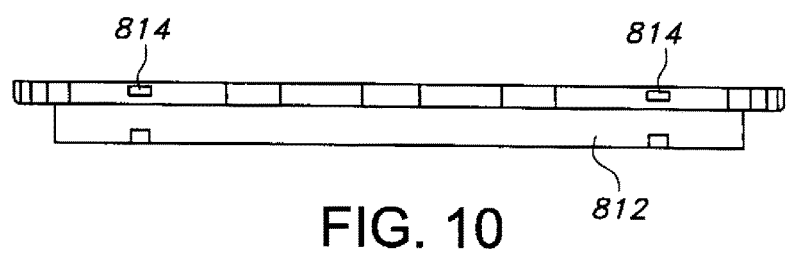
FIG. 10 is an embodiment of the invention showing a side exemplary embodiment of a movable dimensioned grid

Now referring 10 FIGS. 9-10, the movable dimensioned grid assembly 800 is shown. FIG. 9 shows a front perspective view of the movable dimensioned grid assembly 800. The inner circular section 802 has a plurality of dimensioned lines relating to surgical variables 807. In one embodiment, the lines are radio-opaque. FIG. 10 shows a side view of the rotating ring 812 with a plurality of apertures or slots 814 configured to accommodate each of the plurality of radial fixturing grips 804 connect to the inner circular section 802. The rotating ring 812 has, a plurality of slots or detents 814, each are sized to retain one of the plurality of radial fixturing grips 804 with an enlarged end 806 to allow planar movement of the inner circular section 802.

Figure 11:
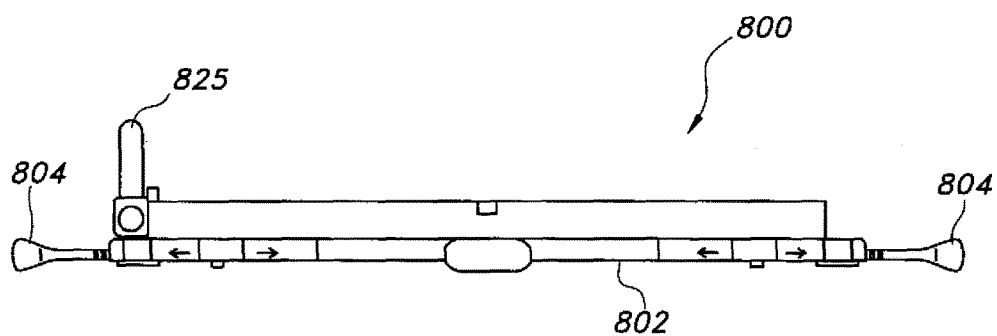
FIG. 11 is an embodiment of the invention showing a side view of an exemplary embodiment of a movable dimensioned grid.
Figure 12:
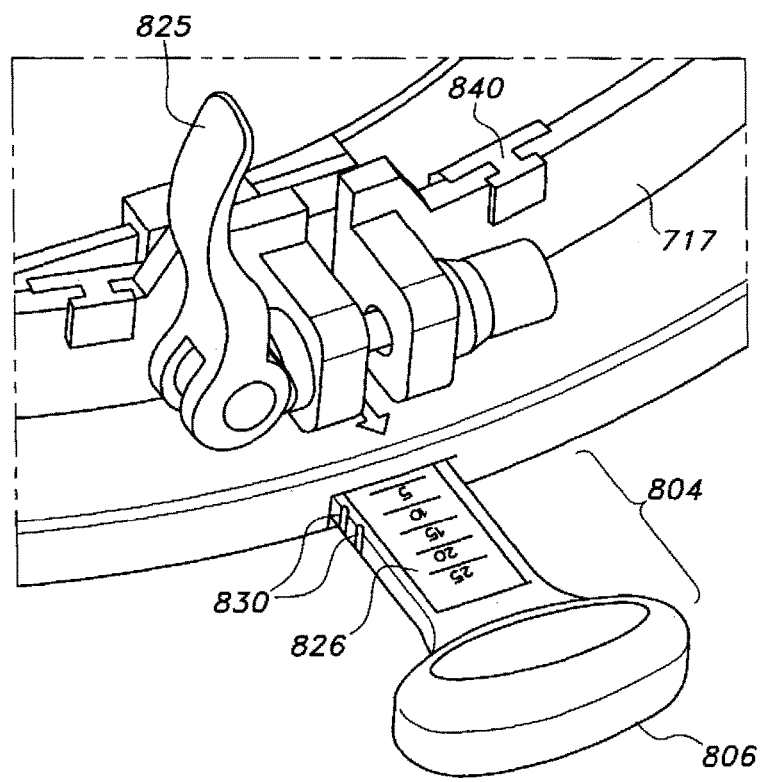
FIG. 12 is an embodiment of the invention showing an exploded view of an exemplary embodiment of a movable dimensioned grid
Figure 13:
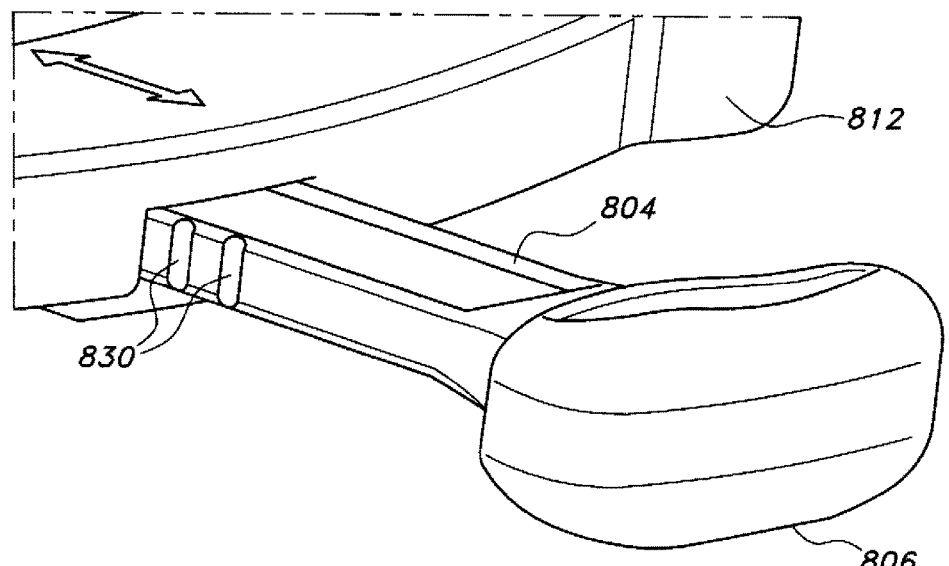
FIG. 13 is an embodiment of the invention showing an exemplary embodiment of a movable dimensioned grid.

Now referring to FIGS. 11-13, exemplary elements of the movable dimensioned grid assembly 800 is shown. FIG. 11 shows a side view of the movable dimensioned grid assembly 800, with an exemplary locking mechanism 825. In this embodiment, the locking mechanism 825 is attached to the fixed ring 717. The locking mechanism 825 allows the fixed ring 717 to be secured to the image intensifier 720, as shown in FIG. 7. When the locking mechanism 825 is released, the movable dimensioned grid assembly 800 can be removed from the image intensifier 720.

FIG. 12, shows an exemplary embodiment, wherein at least one of the plurality of radial fixturing grips 804 has a plurality of markings 826 on each of the plurality of radial fixturing grips 804. The plurality of marking 826 provide a measurement of length. In the preferred embodiment, the range is 5 cm and is centered on 1:2.5 to 0 to 2.5.

In addition to, a plurality of markings 826, the plurality of radial fixturing grips 804, has a controlled motion feature, such as a plurality of notches 830 along the length of each of the plurality of radial fixturing grips 804. The notches 830 facilitate the controlled positioning of the inner circular section 802 of movable dimensioned grid assembly 800 within the view of the C-arm head 720.

Figure 14:
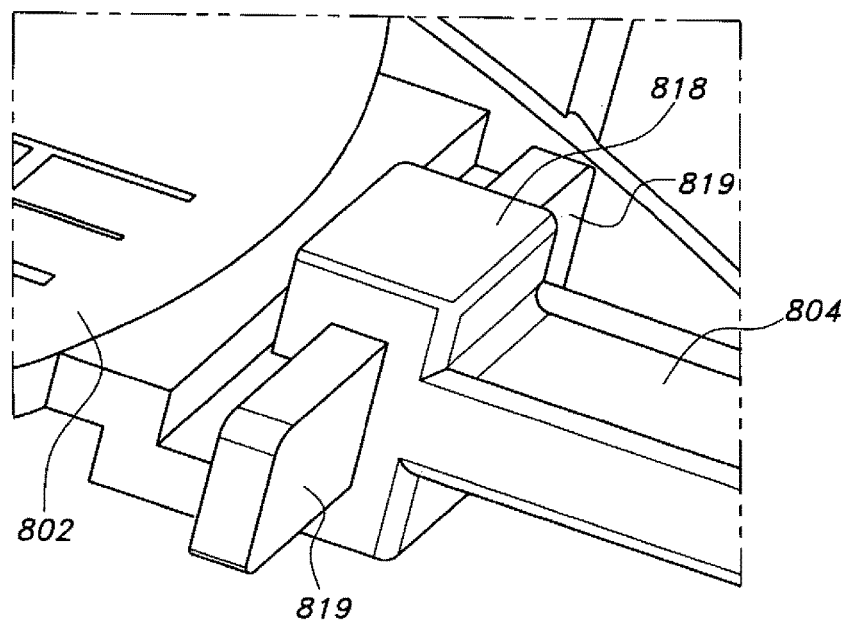
FIG. 14 is an embodiment of the invention showing an exemplary embodiment of a movable dimensioned grid.

Now referring FIG. 14, the plurality of radial fixturing grips 804 connect to the inner circular section 802 by claw, clamp, grip, bracket, track, sliding rail 818. The claw 818 is located on each of the plurality of radial fixturing grips 804 and allows for the inner circular section 802 to translate independently of each perpendicularly opposite radial fixturing grips 804 of the motion desired. A portion of the inner circular section 802 has a fixed bar 819 that fits in the claw 818 and allows translation of the inner circular section 802 thru the claw 818 when the perpendicular opposite radial fixture bar 819 is moved.

Figure 15:
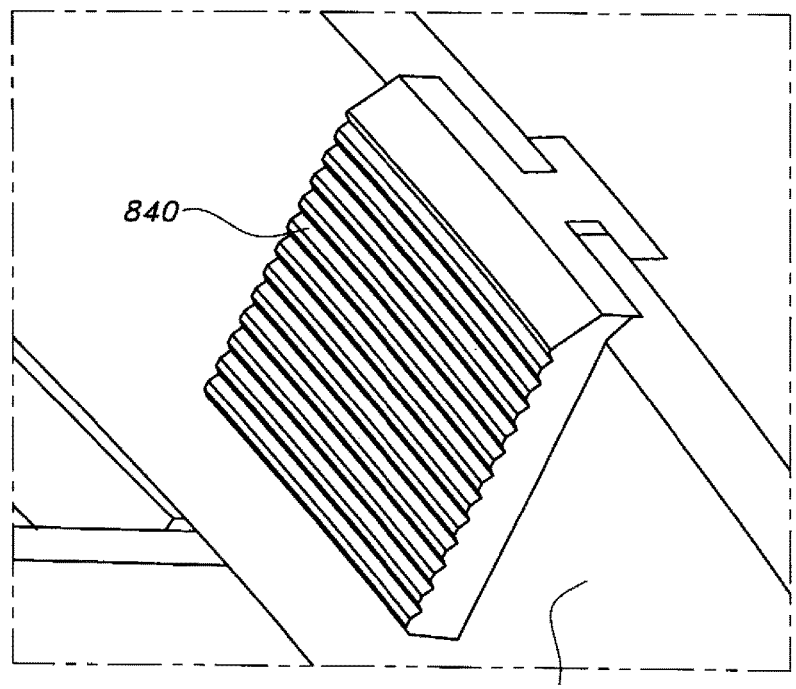
FIG. 15 is an embodiment of the invention showing an exemplary embodiment of a movable dimensioned grid

Now referring FIG. 15, in one exemplary embodiment, a buffer 840 can be positioned on the fixed ring 717, to accommodate different sizes of image intensifier or imaging receiver 720 and assure a secure fit during the procedure.

Figure 16:
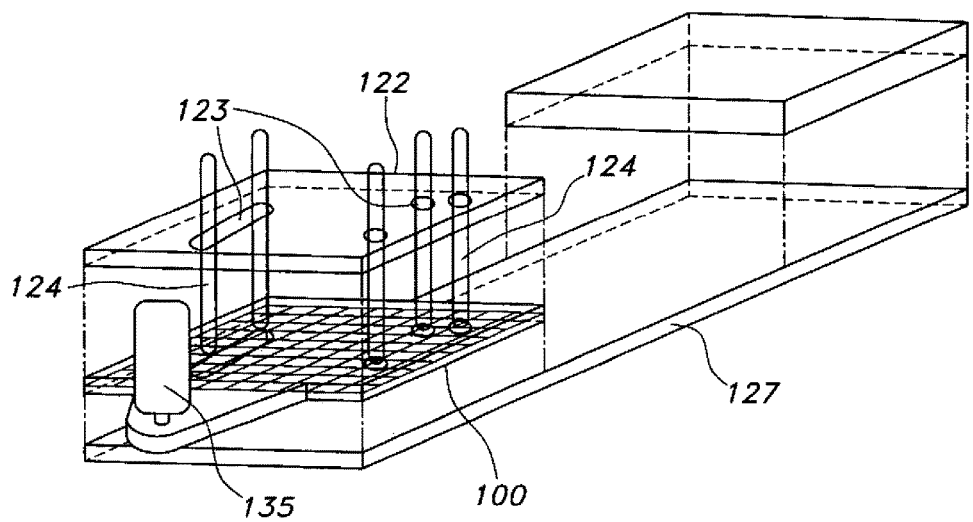
FIG. 16 is a view of the apparatus of the present invention used externally and integrated into the table mat/support system.
Figure 17:
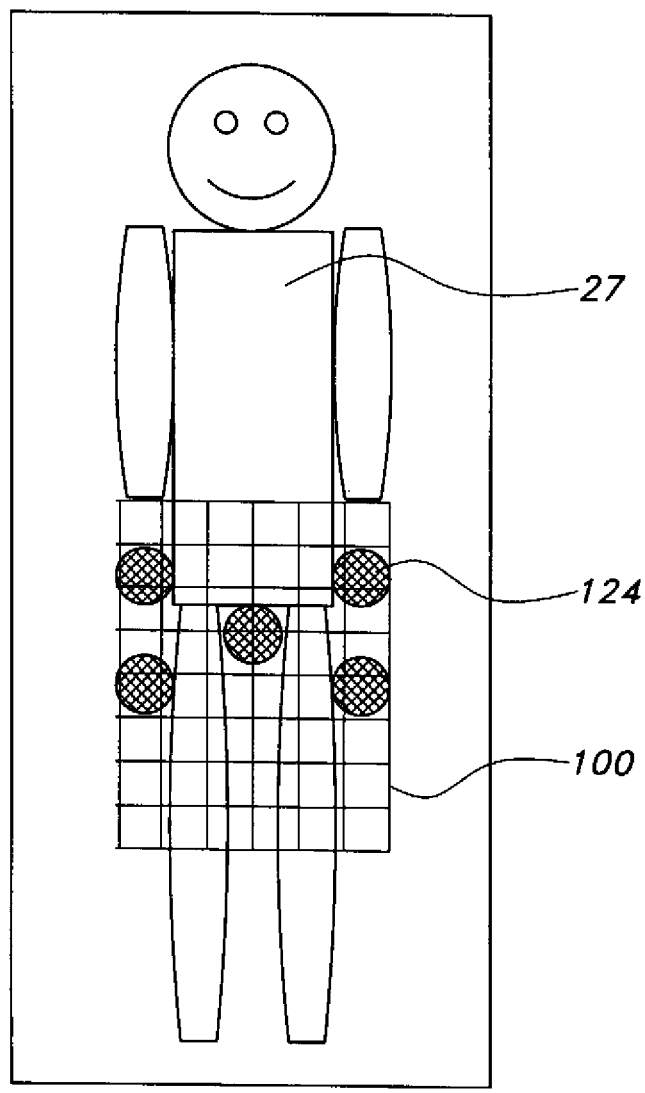
FIG. 17 is a view of the apparatus of the present invention integrated into the procedure table and patient positioning system.

Now referring to FIGS. 16-17 a surgical positioning system made of: a dimensioned grid 100 having a plurality of dimensioned radio-opaque lines corresponding to surgical variables and a substrate, such as an procedure room table 100 connect to or integral with the dimensioned grid 100 is shown. The substrate, such as a procedure table 100 can be for example an procedure room table mat, an procedure room table, a mobile positioning device and a surgical drape. There is a central post 135 on the procedure table. In one embodiment, the dimensioned grid 100 is integrated into and/or manufactured within the procedure room table mat or cover to form a dimensioned grid mat 122. The dimensioned grid 100 can be attached to a substrate, such as a procedure table 100 or a moving table.

The dimensioned grid mat 122 is, manufactured of foam or any procedure room table material that adheres to patient comfort and safety standards. The dimensioned grid mat 122 may be, fixed or connected to the substrate such as procedure table 127, by any method and device to ensure secure fastening and locking of the dimensioned grid mat 122 to the procedure table 127. This may include straps, VELCRO (Velcro Industries B.V.) screws, tie-downs, clamps, and any other fixation or holding jig. Further, this dimensioned grid mat 122 includes any and, all geometries of procedure room table designs. The dimensioned grid mat 122 may be perforated with a plurality of apertures 123 in any pattern that is conducive to allow positioning of the patient by using positioning devices 124 of any geometry. In this embodiment, at least one aperture 123 in the grid 122 is sized to receive or accommodate a positioning device 124. The positioning device 124 projects above the top surface 128 of the mat and is configured to maintain the position of the subject relative to the dimensioned grid 100 or grid mat 122. There is a central post 135 of the procedure table.

The plurality of positioning devices 124 can be used to facilitate the positioning of the dimensioned grid 100 relative to the patient 27. The positioning device 124 are rods or tubes that allow for appropriately positioning and holding the patient 27 securely to allow for accurate imaging and visualization of the patient 27 anatomy relative to the procedure table 127 and dimensioned grid mat 122.

The positioning device 124 can be added to an aperture 123 configured to receive the positioning device 124 or in an alternative embodiment the aperture 123 is configured to accommodate the positioning device 124 and the positioning device 124 is attached to the grid and telescopes out of the aperture 123.

The dimensioned grid 100 has a plurality of dimensioned radio-opaque lines integrated into and/or manufactured within the procedure table 127. In this embodiment, the dimensioned grid mat 122 is connected to the procedure table 127 surface by positioning device 124 that can be manufactured with and include any and all suitable materials. In this embodiment, the procedure table 127 is manufactured of any procedure room table material that adheres to safety standards. The dimensioned grid mat 122 is integrated into the procedure table 127 to form a grid-table assembly 140. In addition, the grid-table assembly 140 may be perforated in any pattern that is conducive to allow appropriate positioning of the patient 27 by using positioning devices of any geometry. The procedure table 127 with integrated dimensioned grid 100 and positioning device can be manufactured with and include any and all suitable materials.

The patient 27 is placed on the dimensioned grid mat 122. The positioning devices 124 are strategically placed at selected locations alongside the patient's 27 body areas according to patient's 27 anatomy and then secured in position within the perforations 123. The plurality of positioning devices 124 can be secured to either the dimensioned grid 100 with a depression in the grid surface or by the use of a clamp or rail.

Figure 18A:
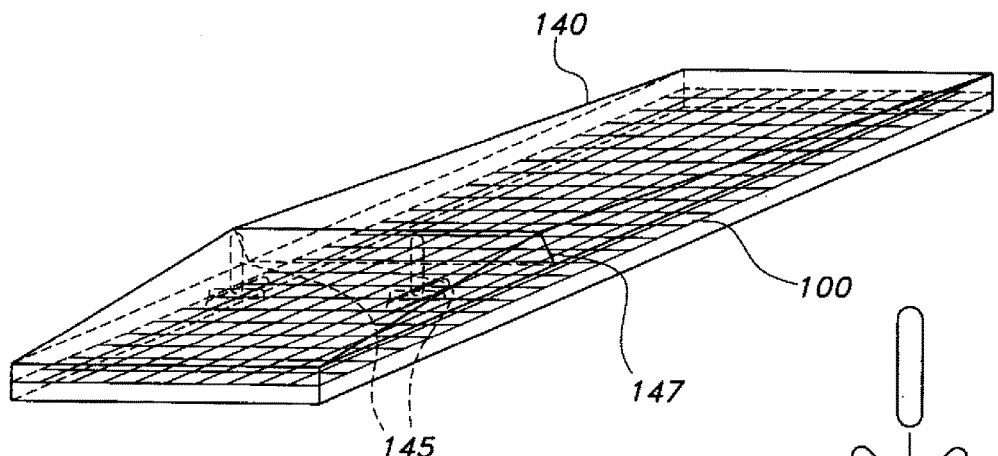
FIG. 18A is an embodiment of the invention showing the relationship of the grid and other associated intra-operative tables and patient positioning equipment.
Figure 18C:
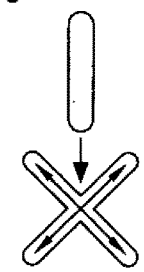
FIG. 18C is an embodiment of the invention showing the relationship of the grid and other associated intra-operative tables and patient positioning equipment.
Figure 18B:
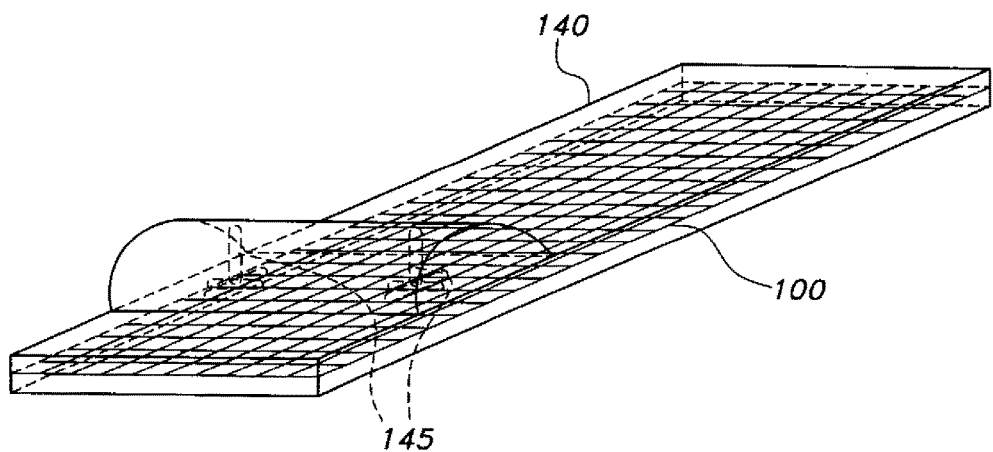
FIG. 18B is an embodiment of the invention showing the relationship of the grid and other associated intra-operative tables and patient positioning equipment.

Now referring to FIGS. 18A-C, further, this grid-table assembly 140 includes any and all geometries of procedure table designs. In this embodiment, a plurality of pegs 145 can be used to facilitate a pelvic tilt or elevated mat 147 that can be used for an anterior approach in order to maintain the correct pelvic orientation. Further, the grid-table assembly 140 can be integrated into the design of the central peg, of the procedure table 127 or any extension of the procedure room table used for an anterior or posterior hip approach or trauma procedure. For example, an internal positioning peg 145 can be used for adapting the basic design for other types of surgery. The peg 145 is formed of upwardly projecting member on a base and is made of a suitable material such as plastic. The material must not be deformable.

In another embodiment, a plurality of pegs 145 can be used to prevent a pelvic collapse during surgery and to maintain pelvic area centered on the procedure table 127, while non-supported parts allow for collapse to help with the stability and comfort. The plurality of pegs 145 can be adjusted to accommodate width and the height of a patient's pelvis. A plurality of pegs 145 can be used to position a flap 147 configures to form a raised area that can stabilize or immobilize a body part during surgery.

Now referring to FIGS. 19 and 20 A-20 B, an, illustrative embodiment of an indicator of a position 950 of a mobile imaging device 161 is shown. The indicator of a position 950 of a mobile imaging device is configured to provide position of the mobile imaging device 161 and provide directional coordinate for a change in position of the mobile imaging device 161 based on coordinate data obtained from the image 953 processed in which the object 960 being imaged is identified in relation to a dimensioned radio-opaque dimensioned grid 100. This coordinate assessment of the object 960 within the field of view in relationship to a dimensioned grid 963 is displayed on the mobile imaging device monitor (FIG. 20B). The processing of the acquired image as shown in FIG. 20B can be achieved either digitally in computer mediated software and a use of a virtual grid or visually by a user. The image of grid 953 is processed to obtain current and desired positioning coordinate data of object 960 in the image's field of view.

The indicator of a position 950 of a mobile device in this embodiment is a navigational mat 952. The navigational mat 952 is positioned under a mobile equipment, such as for example a C-arm device image intensifier 162 to provide a quantifiable assessment of the necessary movements to achieve a more precise 141 position of the C-arm device image intensifier 162 over the patient, based on visual or oral feedback gathered for a size specific image of grid 953 providing coordinate data.

In the exemplary embodiment, a navigational mat 952 is shown providing at least one navigational grid pattern 951. In this exemplary embodiment, two grid patterns are positioned on a navigational mat 952, each of the navigational grid patterns 951 are positioned to rest under the wheels 163 of an imaging device 161 such as a C-arm image intensifier 162 to provide intra-operational procedural navigation.

Now referring to FIG. 20A, a radiopaque dimensioned grid 100 is attached to an, imaging device 161, such as a C-arm device image intensifier 162 (or any X-ray receiver). An object 960 is located on a procedure surface 127. It is imaged and its location in the X-Y plane (plane of the procedure surface 127) is thereby determined. The position of object 960 on procedure surface 127 is determined intra-operatively thru processing of the acquired image (FIG. 20B). A navigational mat 952 is shown providing at least one navigational dimensioned grid pattern 951 which provides the X and V position of the mobile imaging device. Either software or the user can then determine desired coordinate position of object 960. The mobile imaging device 161 is then moved over the navigational mat 952 by using the navigational dimensioned grid pattern 951 by the corresponding amount of X and V that matches the desired coordinates for the object within the image (FIG. 20B). The indicator of a position 950 of a mobile imaging device 161 is configured to provide coordinate data of mobile device 161 either visualized by the user or digitally displayed.

Now referring to FIG. 20B, an image of grid 953 providing coordinate data is shown. Coordinate data means more than one reference point to facilitate the placement of the object 960. However, the desired location of the object 960 is at a location designated by the Δ 962, for which the values X and Y represent the direction of movement of the C-arm image intensifier 162 so that object 960 is in the desired location. The mobile imaging device 161 can move over the floor through coordinate translation X and as shown on mat 952 using wheels 163. The image 953 is processed to obtain current and desired positioning coordinate data of the object being imaged. For purpose of example, if only a translation of Y is desired, the mobile imaging device 161 can be moved, over the indicator of position 950 in the axis provided by the grid pattern 951 visible on the mat 952.

Figure 21:
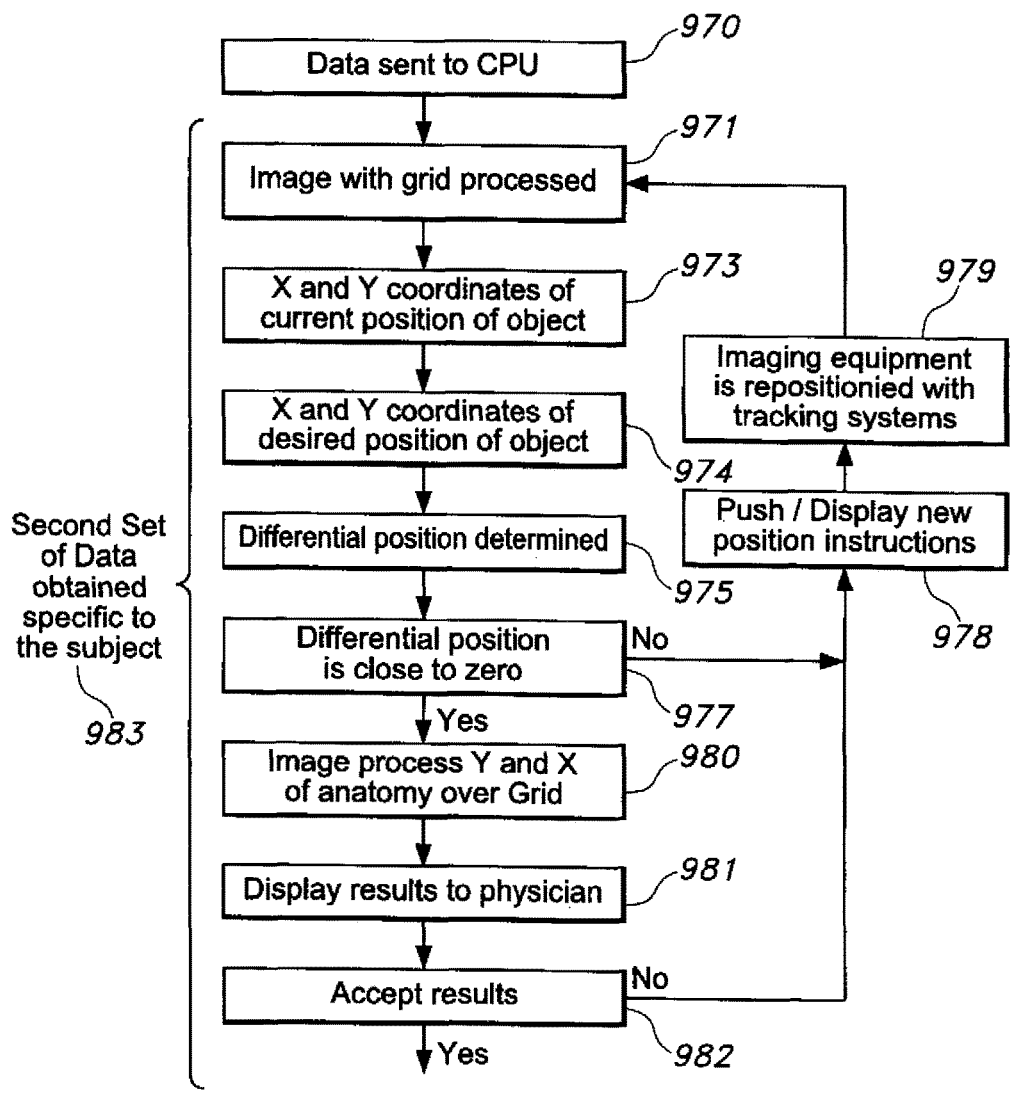
FIG. 21 is a flow chart for the flow of data in exemplary embodiment of a system.

Now referring to FIG. 21, either software or the user can then process the image position of the dimensioned grid 100 according to the flow of data shown. The data, being the digital radiographic image retrieved from the, imaging device 161 is sent to a CPU 970, the image, with grid is processed 971; X and Y coordinates of the current position of the object related to the grid is determined 973, X and Y coordinates of the desired position of the object is determined 974; the differential position is determined 975; determine if the differential position is close to zero 977; if no, push or display new position instructions 978; an imaging device, such as a C arm x-ray machine 162 is repositioned with an indicator of a position 979 of a mobile imaging device 950, such as a navigational mat 952.

If yes, the step of image processing X and Y axis of the anatomy or the prosthesis over the grid 980 occurs. The results are displayed to the physician 981; the next step is to accept the results 982 or the results are not accepted 983 and repeat push or display new position instructions 978; and an imaging device 161, such as a C arm device 162 is repositioned with an indicator of a position of a mobile imaging device 950 such as a navigational mat 952.

Figures 22A, 22B:
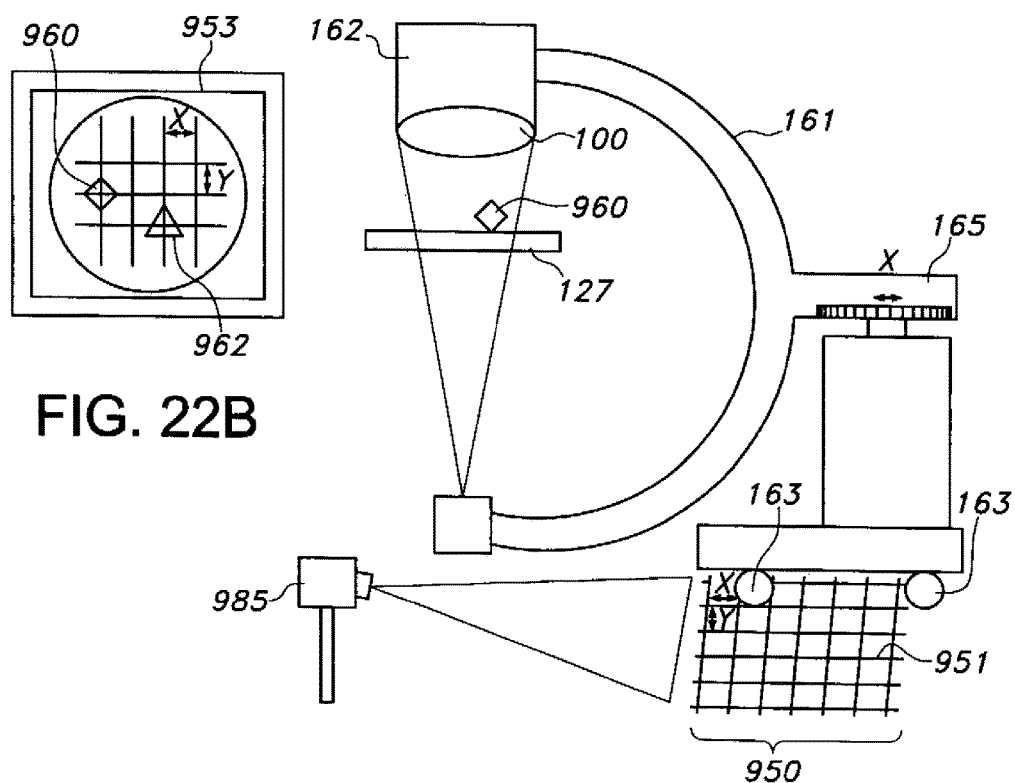
FIG. 22A is are embodiment of the invention showing an exemplary embodiment of a system.
FIG. 22B is an embodiment of the invention showing an exemplary embodiment of a grid image.

Now referring to FIG. 22A a dimensioned grid 100 is attached to a mobile imaging device 161 such as a C-arm X-ray machine image intensifier 162 (or any X-ray receiver). In an alternative embodiment, an indicator of a position of a mobile imaging device 950 is displayed as a mat on the floor by for example a LED or laser generated pattern projector 985. The LED or laser generated pattern projector 985 can be adjusted to display variable dimensions based on pattern and size to provide a quantifiable assessment of the necessary movements to achieve more precise position of the machinery over the patient based on visual or oral feedback gathered from the size specific grid pattern on the image. The position of object 960 is determined intra-operatively, by providing at least one navigational grid pattern 951 showing the X and position and where the object 960 needs to be positioned.

In this exemplary embodiment, a digital source 985 such as a projector shines an indicator of a position of the mobile imaging device 950 such as a navigational mat 952 such as a dimensioned display on the floor by an imaging device, such as a C-arm X-ray machine 162 has mobile features 163, such as wheels. The digital source 985 can be adjusted to display variable dimensions based on pattern or size. Either software or the user can then process the image position of the grid 100. The imaging device 161, such as C-arm X-ray machine 162 is then moved to the desired coordinates. An object 960 is located on a procedure surface 127. It is imaged, and its location in the X-Y plane (plane of the procedure surface 127) is thereby determined.

Now referring to FIG. 22B, an image 953 of the movable dimensioned providing coordinate data is shown. However, the desired location of the object 960 is at a location designated by the Δ 962, for which the values X and Y represent the direction of movement of the an imaging device 161, such as a C-arm machine 162 so that object 960 is in the desired location. The imaging, device 161, such as C-arm device 162 can move over the floor through coordinate translation X and V as shown by the digital pattern 950 displayed by the projector source 985. For example. If only a translation of Y is desired, the C arm machine 161 can be moved through length by rolling wheels 163 by referencing its position on the projected digital display 950 in order to place object 960 in the desired location Δ 962.

The digital source 985 such as a projector shines an indicator of a position of the mobile imaging device 950 such as a navigational mat 952 such as a dimensioned display on the floor nearby an imaging device, such as a C-arm X-ray machine 162 has mobile features 163, such as wheels, to provide a quantifiable assessment of the necessary movements to achieve a more precise position of the C-arm device image intensifier 162 over the patient, based on visual or oral feedback gathered for a size specific grid pattern of the image, ie coordinate data as shown as an image 953.

Figures 23A, 23B:
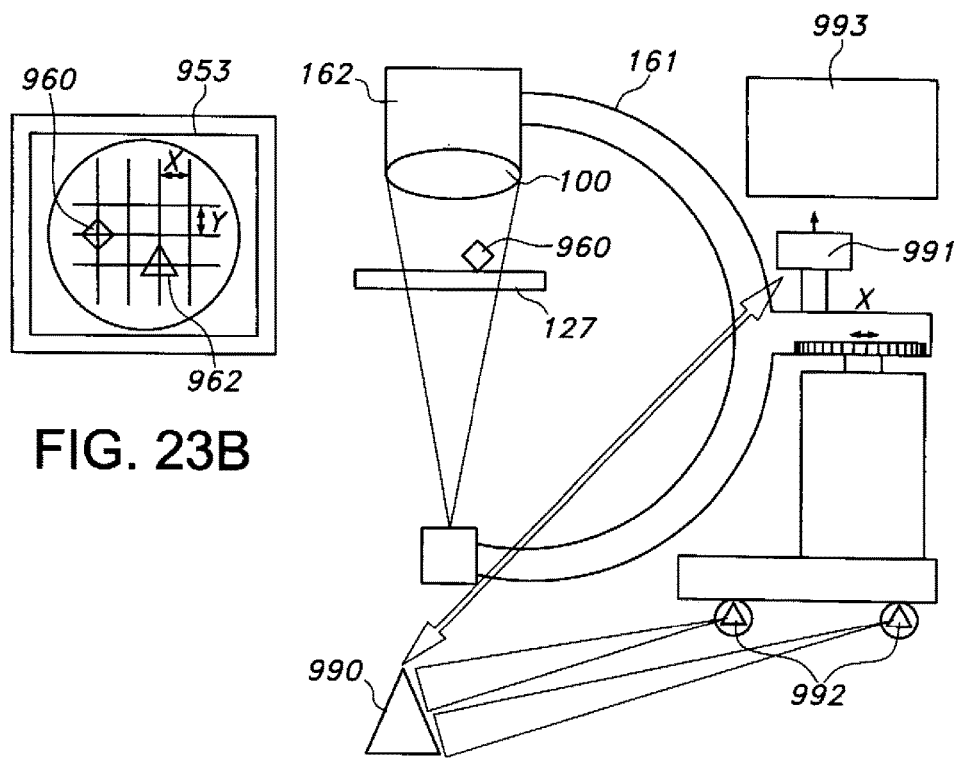
FIG. 23A is an embodiment of the invention showing an exemplary embodiment of a system.
FIG. 23B is an embodiment of the invention shoving an exemplary embodiment of a grid image.

Now referring to FIG. 23A, a device, such as a monitor 991 or 993 (zoomed out view of monitor 991) that displays to the user the amount of movement of a mobile piece of machinery used in a procedure room such as a c-arm 162. The movement is quantified by a tracking device 992 mounted inside or outside the machine moveable part (like wheels or rails) or using a positioning tracking device, wireless or not 990.

Once the desired position 962 of the object 960 is identified in FIG. 238, the differential of coordinate X and Y is determined and the software sends the desired movement to the base of the positioning tracking system 990. The positioning tracking system provides live monitoring of movements to the user via a display 991/993. The movements of the mobile machine are captured by the sensors 992 placed either in the wheels or independently position on the machine. The sensors 992 communicate information wirelessly to the positioning tracking systems 990 which communicates wirelessly with the receiver part of the monitor 991/993 so as to display the results. The movement can be either displayed on a monitor 991 and 993 for live navigation or set based on a preprogrammed preferred output such as countdown to "destination" or a saved location. A preferred location can be saved from the live navigation in order to return to it at a later part of a procedure. These locations and distances can be pre-programmed based on data extrapolated directly or indirectly from the image grid 953.

Now referring to FIG. 23B, an image of grid 953 providing coordinate data is shown. However, the desired location of the object 960 is at a location designated by the Δ 962, for which the values X and Y represent the direction of movement of the an imaging device 161, such as a C-arm machine so that object 960 is in the desired location. The imaging device 161, such as C-arm machine can move over the floor through coordinate translation X and Y as shown on the display monitor 991 and 993. If only a translation of Y is desired, the wheels 992 of the C-arm 161 can be moved through length Y to place object 960 in the desired location Δ 962. In the exemplary embodiment shown in FIG. 24A, a motion detector 990, such as a wireless global positioning system is situated in a procedure room and a mobile wireless device 991 is located in the imaging device 161, such as C-arm machine, is tracked wirelessly by a motion detector 990 and the mobile device 991, providing X and Y distances or locations wirelessly. A display 993 can show the X and Y movements which are needed to place the object 960 in the desired location.

Now referring to FIG. 23B, an image of grid 953 providing coordinate data is shown. However, the desired location of the object 960 is at a location designated by the Δ 962, for which the values X and Y represent the direction of movement of the C-arm machine 161 so that object 960 is in the desired location. The C-arm machine 162 can move over the floor through coordinate translation X and Y. If only a translation of X is desired, the C arm mount 965 can be moved through length X to place object 960 in the desisted location Δ 962.

Figure 24B:
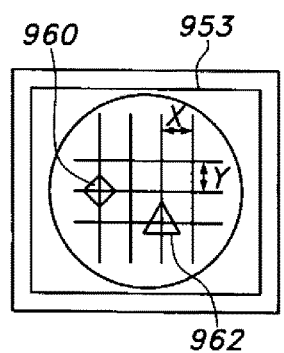
FIG. 24B is an embodiment of the invention showing an exemplary embodiment of a grid image.
Figure 24A:
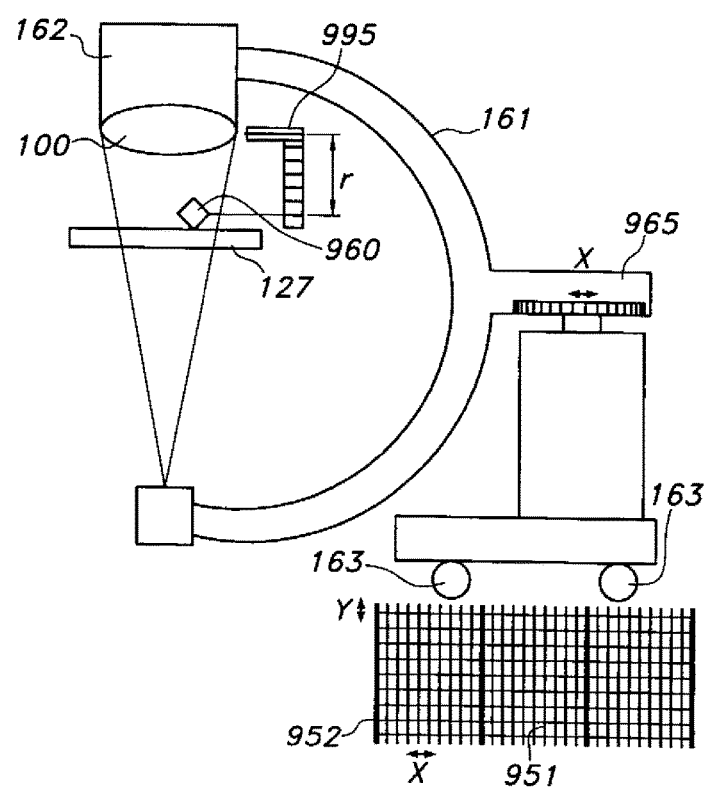
FIG. 24A is an embodiment of the invention showing an exemplary embodiment of a system.

Now referring to FIG. 24A, a magnification finder 995, using either analog (ruler 995) or digital distance/range finder (ultrasonic, optical or laser), capture the distance between the image intensifier and the plane of the object. That distance r is used to determine the magnification ratio of at the place of the object This adjusts the coordinate information to scale based on a correction for magnification. The magnification finder 995 is based on the specific dimensions of a particular mobile an imaging device 161, by identification of the distance from the image intensifier, such as on a C-arm device 162 to a specific anatomical landmark on an object, such as a patient interoperatively in order to assess the amount of magnification in the image reviewed by the surgeon for both quantitative analysis and navigational purposes.

The magnification finder 995 provides a quantifiable assessment of the necessary movements to achieve a more precise position of the C-arm device image intensifier 162 over the patient, based on visual or oral feedback gathered for a size specific grid pattern of the image, is coordinate data 953.

Figure 25:
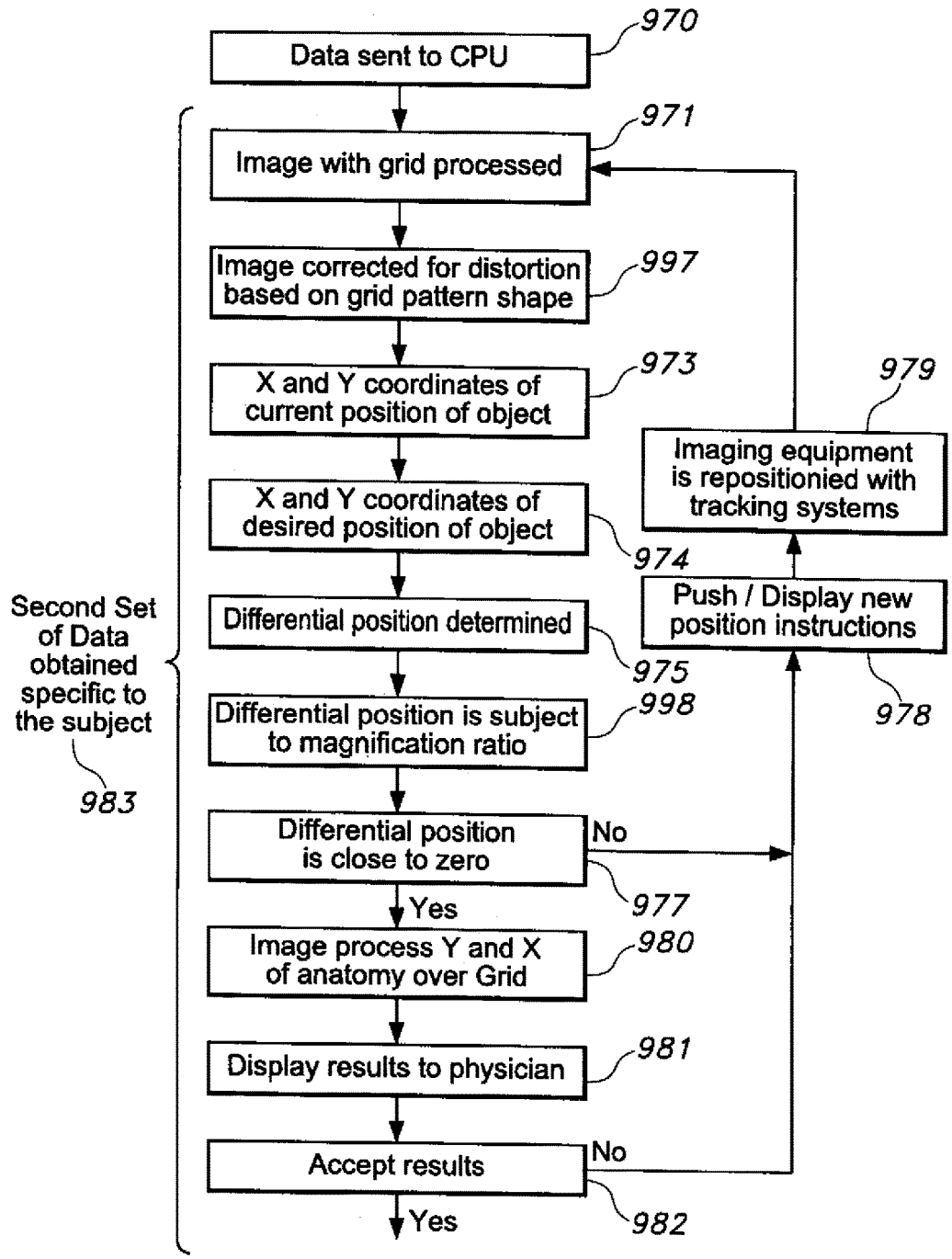
FIG. 25 is a flow chart for the flow of data in exemplary embodiment of a system.

Now referring to FIG. 25, either software or the user can then process the image position of the dimensioned grid 100 according to the flow of data shown. The data is sent to a CPU 970, the image with grid and magnification ratios are processed 971; the image is corrected for distortion based on the grid pattern shape 997; X and Y coordinates of the current position of the object is determined 973, X and Y coordinates of the desired position of the object is determined 974; the differential position is determined 975; the differential position is subjected to the magnification ratio 998; determine if the differential position is close to zero 977; if no, push or display new position instructions 978; and imaging device 161, such as a C arm device, is repositioned a with an indicator of a position of a mobile imaging device 950, such as a navigational mat 952 or a positioning tracking system (990/991/992/993).

If yes, the step of image processing X and Y axis of the anatomy or the prosthesis over the grid 980 occurs. The results are displayed to the physician 981; the next step is to accept the results 982 or the results are not accepted 983 and repeat push or display new position instructions 978; and imaging equipment, such as a C Arm device 162 is repositioned with an indicator of a position of a mobile imaging device 950 such as a navigational mat 952 or a positioning tracking system (990/991/992/993).

The anatomical image captured from an imaging system is processed with an analogue or digital (software generated virtual grid) grid and corrected for distortion/parallax that is inherent in imaging systems. This distortion correction method can be any available technique and uniquely applied to the use of a grid (analogue or virtual) with this surgical positioning system.

Use of radio-opaque ink methods (pad, sheet printing) and technology (medical inks, metal inks, tungsten inks), or templating and stenciling methods, to print a grid pattern with surgical variables for use in any musculoskeletal surgical procedure-particularly, hip replacement, shoulder replacement, knee replacement, and all bone fracture reductions for example a tibial fracture is shown. The radiopaque ink printing is applied to any suitable and appropriate substrate such as acrylic, polycarbonate, polypropylene, or polyethylene materials.

While the invention has been described with reference to preferred and example embodiments, it will be understood by those skilled in the art that, a variety of modifications, additions and deletions are within the scope of the invention, as defined by the following claims.

The invention claimed is:

1. A movable surgical positioning device comprising: a movable inner circular section having a radio-opaque grid pattern corresponding to anatomical landmarks related to a surgical procedure a plurality of radial fixturing grips attached to the inner section, each of said radial fixturing grips being configured to allow planer movement of the inner circular section; said inner circular section positioned within an outer rotatable ring wherein said outer rotatable ring further comprises a plurality of slots positioned to retain each of said radial fixturing grips.

2. The movable surgical positioning device of claim 1 wherein at least one of the plurality of radial fixturing grips has a plurality of markings that provide a measurement of length.

3. The movable surgical positioning device of claim 2, wherein the retaining member further comprising a pressing plate configured to retain the movable inner circular section and the rotating ring.

4. The movable surgical positioning device of claim 2 wherein the inner section has a plurality of bars and each of the plurality of radial fixturing grips has a claw configured to receive one of the plurality of bars.

5. The movable surgical positioning device of claim 1 further comprising a locking mechanism positioned to retain the movable dimensioned grid in a fixed position.

6. The movable surgical positioning device of claim 1 wherein the radio-opaque grid pattern shows surgical reference angles.

7. The movable surgical positioning device of claim 1 further comprising a fixed ring configured to connect to an image intensifier of a radiographic imaging device.

8. The movable surgical positioning device of claim 7 wherein the fixed ring is configured to connect to the rotating ring.

9. The movable surgical positioning device of claim 1 wherein the radio-opaque grid pattern shows length positioning.

10. The movable surgical positioning device of claim 1 wherein the radio-opaque grid pattern shows targeting.

* * * * *